(12) United States Patent
Tulin

(10) Patent No.: US 10,472,664 B2
(45) Date of Patent: Nov. 12, 2019

(54) SCREENING ASSAY FOR IDENTIFICATION OF POLY(ADP-RIBOSE) POLYMERASE 1 INHIBITORS

(71) Applicant: Institute for Cancer Research, Philadelphia, PA (US)

(72) Inventor: Alexei Tulin, Philadelphia, PA (US)

(73) Assignee: Institute For Cancer Research, Philadelphia, PA (US)

( * ) Notice: Subject to any disclaimer, the term of this patent is extended or adjusted under 35 U.S.C. 154(b) by 746 days.

(21) Appl. No.: 14/870,516

(22) Filed: Sep. 30, 2015

(65) Prior Publication Data

US 2016/0097083 A1   Apr. 7, 2016

Related U.S. Application Data

(60) Provisional application No. 62/059,203, filed on Oct. 3, 2014.

(51) Int. Cl.
| | |
|---|---|
| C12Q 1/48 | (2006.01) |
| G01N 33/573 | (2006.01) |
| C12N 9/10 | (2006.01) |
| C12N 9/00 | (2006.01) |

(52) U.S. Cl.
CPC ............... *C12Q 1/48* (2013.01); *C12N 9/00* (2013.01); *C12N 9/10* (2013.01); *G01N 33/573* (2013.01); *G01N 2333/4703* (2013.01); *G01N 2333/91142* (2013.01); *G01N 2500/02* (2013.01); *G01N 2500/20* (2013.01)

(58) Field of Classification Search
None
See application file for complete search history.

(56) References Cited

U.S. PATENT DOCUMENTS

2009/0176765 A1   7/2009   Jones et al.
2009/0227590 A1   9/2009   Press et al.

OTHER PUBLICATIONS

Kotova et al.; Methods Mol Biol.; 2011; 780:491-516.*
International Search Report and Written Opinion dated Mar. 4, 2016 issued in related application PCT/US15/53259.
PubChem CID 10940—Create Date: Aug. 8, 2005.
PubChem CID 3260917—Create Date: Sep. 6, 2005.
PubChem CID 5094348—Create Date: Sep. 18, 2005.
PubChem CID 770075—Create Date: Jul. 8, 2005.

* cited by examiner

*Primary Examiner* — Allison M Fox
*Assistant Examiner* — Qing Xu
(74) *Attorney, Agent, or Firm* — Stradley Ronon Stevens & Young, LLP

(57) ABSTRACT

Screening methods as well as systems and kits for identifying inhibitors of DNA-independent, histone H4-dependent activation of PARP-1 are provided. The methods comprise screening molecules for their capacity to inhibit the activation and/or biologic activity of PARP-1, as measured by poly(ADP)-ribose production from nicotinamide adenine dinucleotide. PARP-1 inhibitors identified through the screening methods may be used to treat cancer in which PARP-1 activation or biologic activity plays a role.

10 Claims, 5 Drawing Sheets

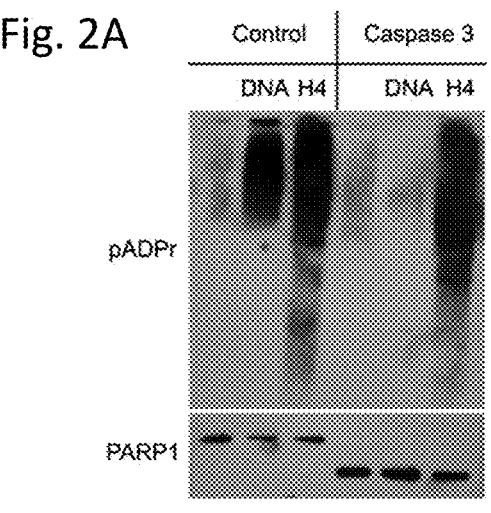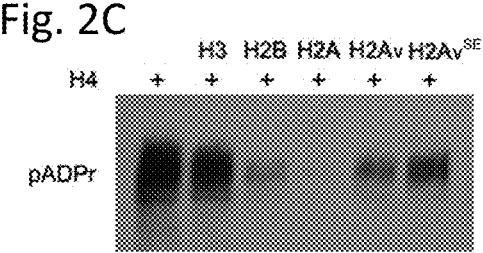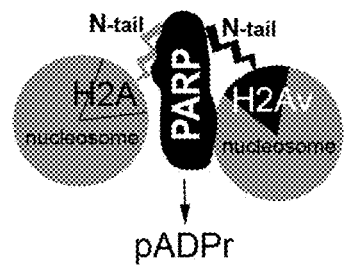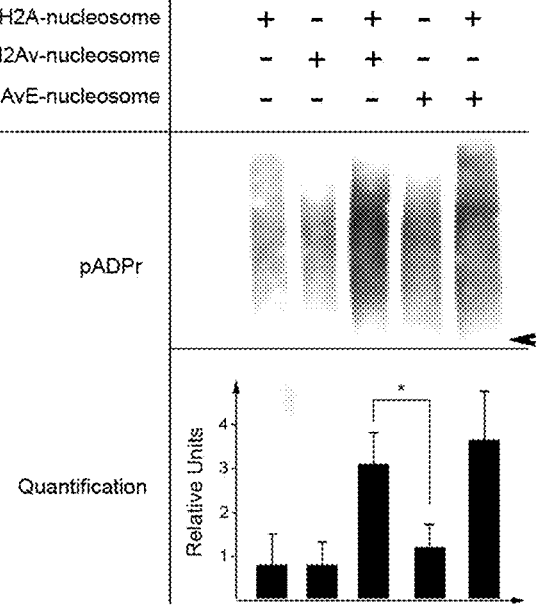

Fig. 3A
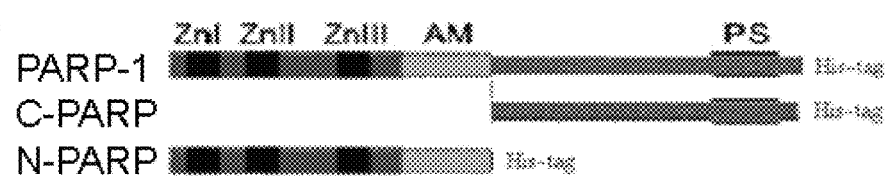
Fig. 3B
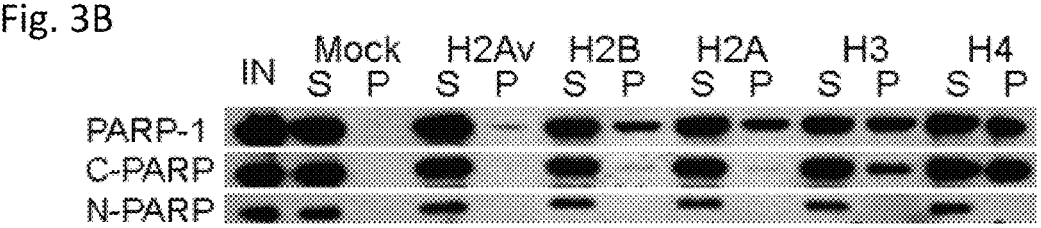
Fig. 3C                                                                 Fig. 3D
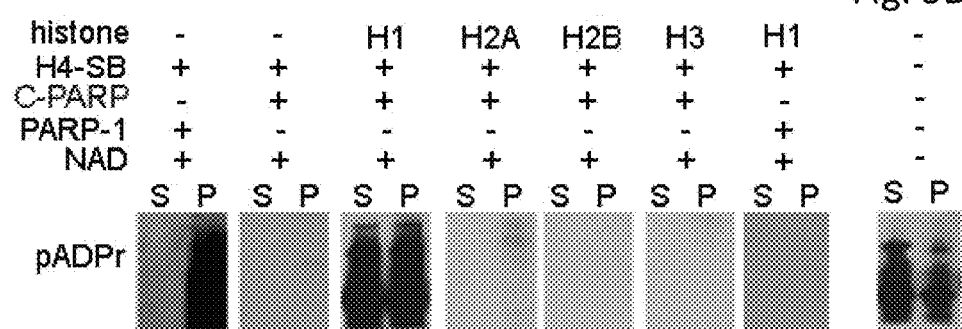

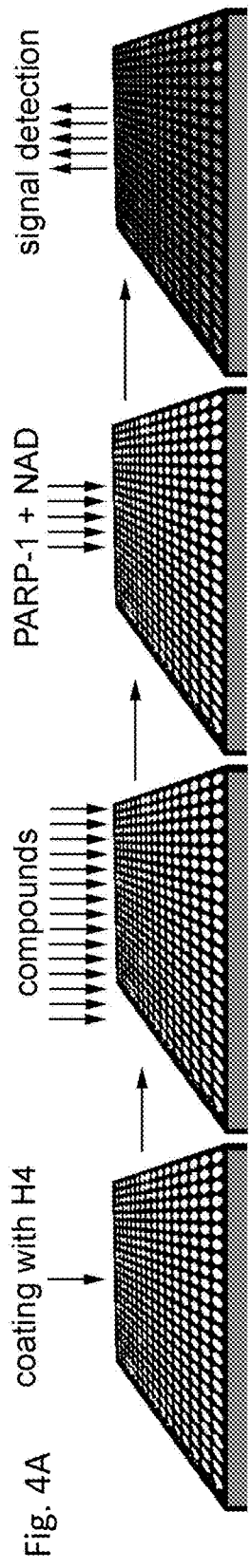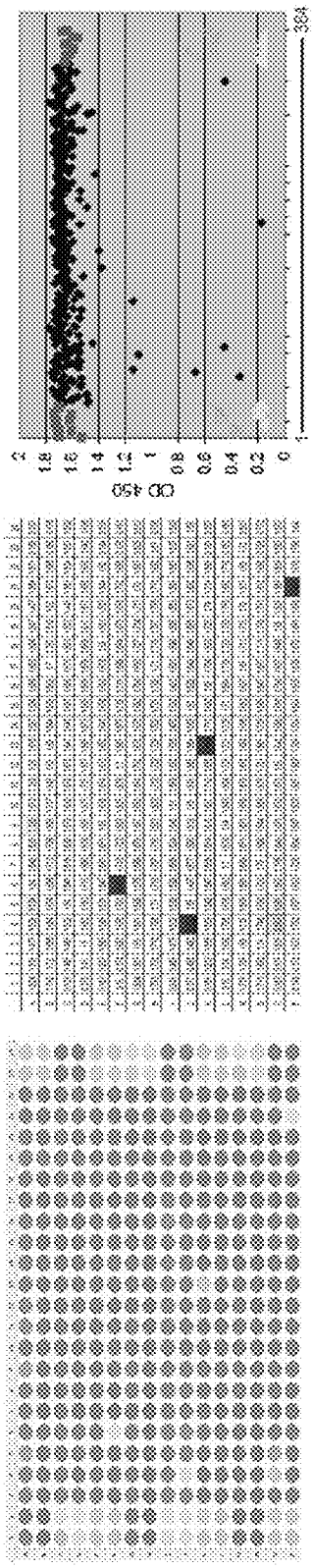
Fig. 4A  Fig. 4B  Fig. 4C  Fig. 4D

SCREENING ASSAY FOR IDENTIFICATION OF POLY(ADP-RIBOSE) POLYMERASE 1 INHIBITORS

CROSS REFERENCE TO RELATED APPLICATIONS

This application claims priority to U.S. Provisional Application No. 62/059,203, filed on Oct. 3, 2014, the contents of which are incorporated by reference herein, in their entirety and for all purposes.

FIELD OF THE INVENTION

The invention relates generally to the field of in vitro screening assays. More particularly, the invention relates to a cell-free assay, which takes advantage of the histone H4-dependent activation of poly(ADP-ribose) polymerase 1 (PARP-1) whereby compounds or compositions are evaluated for their capacity to inhibit histone H4-related activation of PARP-1.

BACKGROUND OF THE INVENTION

Various publications, including patents, published applications, technical articles and scholarly articles are cited throughout the specification. Each of these cited publications is incorporated by reference herein, in its entirety and for all purposes.

The poly ADP-ribose (ADPr) polymerase, PARP-1, is an essential protein involved in a wide range of cellular functions, including genotoxic stress response, transcription activation, cellular differentiation, DNA-repair, among others. On the molecular level, PARP-1 binds to DNA and catalyzes the transfer of ADPr and de novo synthesis of poly ADPr by utilizing the glycolytic intermediate nicotinamide adenine dinucleotide (NAD+) as a substrate. PARP-1 modifies itself and modifies its target proteins by adding ADPr to glutamic residues. The addition of ADPr polymers regulates the catalytic and DNA binding activity of PARP1 as well as the cellular activity and localization of its target proteins.

It was previously determined that PARP-1 enzymatic activity is required for normal assembly of higher-order chromatin structures as well as for the transcriptional activation of heat-shock-dependent, NF-kB-dependent, ecdysteroid-dependent, and ribosomal genes. These studies demonstrated that PARP-1 regulates the transcription of these genes by inducing chromatin loosening at targeted genetic loci. These roles are distinct from the previously characterized roles of PARP-1 in DNA repair and apoptosis.

PARP-1 inhibitors have been shown to selectively eliminate several types of tumorigenic cells. In recent years, PARP-1 inhibitors became popular in clinical research on novel strategies of cancer treatment and, a number of PARP-1 inhibitors are currently undergoing clinical trials for treatment of genetically disposed mutant tumors. Unfortunately, a number of clinical studies reported setbacks in research on PARP-1-based anticancer therapies.

One of the factors that may limit the potency of PARP-1 inhibitors is the majority of currently available inhibitors were designed as NAD competitors. NAD is abundant, ubiquitous, and is used by many other enzymes. Therefore, it is very difficult to completely eliminate NAD interaction with PARP-1 without drastically affecting other metabolic processes. Moreover, as classical PARP-1 inhibitors demonstrate substantial similarities to nucleotide analogues, they obstruct functions of enzymes which utilizing nucleotides as cofactors, such as kinases.

As PARP-1 remains a viable target in cancer therapy, there remains a need for PARP-1 inhibitors that do not affect other enzymes or other normal metabolic processes. Relatedly, there remains a need for PARP-1 inhibitors that diverge from the established model of aiming at the NAD-PARP-1 interaction.

SUMMARY OF THE INVENTION

In some aspects, the disclosure features methods for screening a compound for capability to inhibit poly(ADP-ribose) polymerase 1 (PARP-1). The methods generally comprise contacting PARP-1 or a portion of PARP-1 comprising the catalytic domain with the core histone H4 in the presence of a compound and nicotinamide adenine dinucleotide, and determining the level of H4-dependent biologic activity of the PARP-1 or the portion of PARP-1 comprising the catalytic domain in the presence of the compound relative to the level of H4-dependent biologic activity of the PARP-1 or a portion of PARP-1 comprising the catalytic domain in the absence of the compound. Histone H4 may be affixed to a support. In some aspects, the PARP-1 or a portion of PARP-1 comprising the catalytic domain is free of DNA. The PARP-1 may comprise human PARP-1. The portion of PARP-1 comprising the catalytic domain may comprise a portion of human PARP-1 comprising the catalytic domain.

The compound may be contacted with the PARP-1 or the portion of PARP-1 comprising the catalytic domain prior to contacting the PARP-1 or the portion of PARP-1 comprising the catalytic domain with the core histone H4. The core histone H4 may be contacted with the compound prior to contacting the PARP-1 or the portion of PARP-1 comprising the catalytic domain with the core histone H4.

Determining of the level of H4-dependent biologic activity of the PARP-1 or the portion of PARP-1 comprising the catalytic domain may comprise determining the level of poly(ADP)-ribose produced by the PARP-1 or the portion of PARP-1 comprising the catalytic domain. Determining the level of poly(ADP)-ribose may comprise quantifying the level of poly(ADP)-ribose. Determining the level of poly (ADP)-ribose may comprise measuring light absorbance at 450 nm or 650 nm.

The disclosure also features kits for screening compounds for capability to inhibit PARP-1. The kits comprise PARP-1 or a portion of PARP-1 comprising the catalytic domain, nicotinamide adenine dinucleotide, the core histone H4, and instructions for using the PARP-1 or portion of PARP-1 comprising the catalytic domain, the nicotinamide adenine dinucleotide, and the core histone H4 in a method for screening a compound for capability to inhibit PARP-1. The kit may further comprise a support. The core histone H4 may be affixed to a support. A support may comprise a plate comprising a plurality of wells. The kits may comprise controls, for example, a compound that inhibits the H4-dependent activation of PARP-1 and/or a compound that does not inhibit the H4-dependent activation of PARP-1. In some aspects, the PARP-1 or a portion of PARP-1 comprising the catalytic domain is free of DNA.

The disclosure also features methods for detecting and/or quantifying PARP-1 in a sample. The methods generally comprise contacting the sample with the core histone H4 in the presence of nicotinamide adenine dinucleotide, and determining the level of H4-dependent biologic activity of PARP-1 in the sample. The core histone H4 may be affixed to a support. Determining the level of H4-dependent biologic activity of PARP-1 may comprise determining the level of poly(ADP)-ribose. Determining the level of poly(ADP)-ribose may comprise measuring light absorbance at 450 nm or 650 nm.

The sample may comprise a cell extract. The cell extract may comprise a cancer cell extract. The cancer cell extract may comprise a prostate cancer cell extract, a kidney cancer cell extract, a breast cancer cell extract, a leukemia cell extract, a melanoma cell extract, a lymphoma cell extract, a glioblastoma cell extract, or an ovarian cancer cell extract.

The disclosure also features methods for determining the synthesis of poly(ADP-ribose) in a sample comprising PARP-1 or believed to comprise PARP-1. In general, the methods comprise contacting the sample with the core histone H4 in the presence of nicotinamide adenine dinucleotide, and determining the level of poly(ADP)-ribose in the sample. The core histone H4 may be affixed to a support. Determining the level of poly(ADP)-ribose may comprise measuring light absorbance at 450 nm or 650 nm. The sample may comprise a cell extract. The cell extract may comprise a cancer cell extract. The cancer cell extract may comprise a prostate cancer cell extract, a kidney cancer cell extract, a breast cancer cell extract, a leukemia cell extract, a melanoma cell extract, a lymphoma cell extract, a glioblastoma cell extract, or an ovarian cancer cell extract.

BRIEF DESCRIPTION OF THE DRAWINGS

FIGS. 2A-D show PARP-1 protein regulation by histones (poly(ADP-ribose) polymer is denoted "pADPr"). FIG. 2A shows interaction with purified core histone H4 activates PARP-1 in a DNA-independent manner. Full-length PARP-1 protein (left) and PARP-1 protein cleaved by Caspase 3 (right) were pre-incubated with randomly broken DNA or core histone H4, followed by mixing with NAD. The products of PARP-1 enzymatic activity, poly(ADP-ribose), were detected after PAGE on a Western blot using the anti-pADPr antibody. These data clearly demonstrate that the DNA-binding domain of PARP-1 is not required for histone-dependent PARP-1 activation. FIG. 2B shows interaction with purified histones H2Av and H2AvSE does not activate PARP-1 in vitro. FIG. 2C shows the inhibitory effects of H2A, H2Av, and H2AvSE on PARP-1 in vitro: Purified core histone H2A completely inhibits H4-dependent PARP-1 activation, while H2Av and H2AvSE do not block H4-dependent PARP-1 activation. FIG. 2D shows PARP-1 enzymatic activity is stimulated by H2Av-containing nucleosomes in the presence of an equimolar amount of the wild-type nucleosome. PARP-1 was pre-incubated with different coregulators, followed by mixing with NAD. The amount of the product of PARP-1 enzymatic activity, poly(ADP-ribose), was detected after PAGE on a Western blot using the anti-Change(s) pADPr antibody and quantified independently using the Image Quant.

FIGS. 3A-C show H4-dependent PARP-1 activation requires only catalytic domain of PARP-1. FIG. 3A shows a domain structure comparison for PARP-1 and deletion isoforms N-PARP and C-PARP. The domains include zinc fingers (ZnI-III), automodification domain (AM), and (PS)—PARP-1 catalytic site. FIG. 3B shows a binding assay between histone-coupled beads and PARP-1 deletion isoforms; IgG proteins were detected after PAGE on a Western blot using anti-His-tag antibody. The binding control IgG protein was detected using anti-rabbit antibody. FIG. 3C shows binding-activity assay: either full-length PARP-1 or deletion isoform C-PARP was incubated with H4-coupled sepharose beads (H4-BS), washed, and later mixed with NAD and other histones (H1, H2A, H2B, and H3) to induce poly(ADP-ribose) (pADPr) production. The supernatant (S) was removed, and the pellet (P) was washed. The absence of AM domain in C-PARP resulted in the addition of H1 as a substrate for poly(ADP-ribosyl)ation. D. Binding assay: the supernatant from a binding-activity assay containing poly-ADP-ribosylated H1 was taken and incubated with new H4-coupled beads.

FIGS. 4A-D show a screening strategy for the identification of PARP-1 inhibitors. FIG. 4A shows a schematic representation of the pipeline used for the identification of PARP-1 inhibitors. FIGS. 4B-D show that data were visualized in a color-coded table representing a 384 well plate, in which potential inhibitors would be identified according to signal strength (poly(ADP-ribose) (pADPr) signal) (FIG. 4B) or as a table with the number reflecting the actual signal strength (e.g., absorbance in nm) (FIG. 4C) or as a graph representing the signal as positive or negative (or relatively so) in relation to controls.

In FIG. 5B, the star symbolizes PARP-1 activation by interaction with H4, with biologic activity upregulated as symbolized by the wavy lines emanating from PARP-1 (poly(ADP-ribose) polymer is denoted "pADPr").

DETAILED DESCRIPTION OF THE INVENTION

Figure 1:
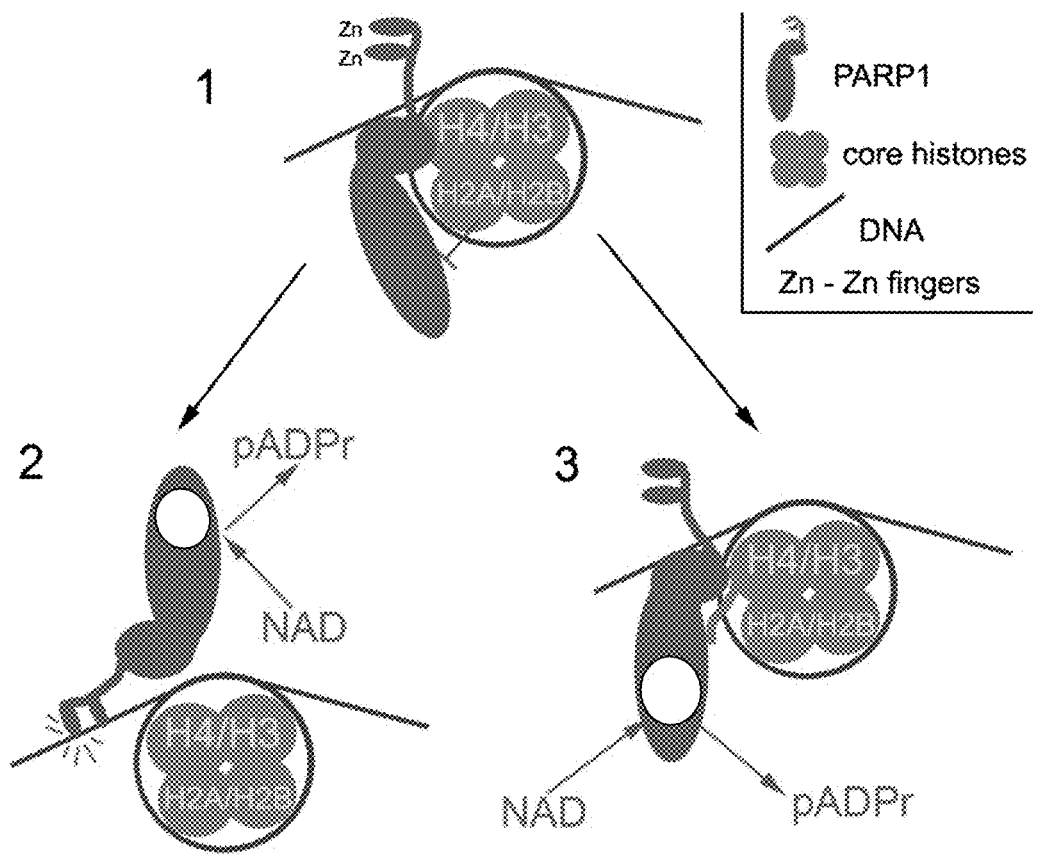
FIG. 1 shows a model of the regulation of PARP-1 protein enzymatic activity in chromatin. Part 1 shows PARP-1 protein is broadly distributed in chromatin due to interaction with core histones in the context of nucleosome. PARP-1 is inactive in this state because of inhibitory effect of histone H2A. Part 2 shows genotoxic stress-dependent PARP-1 activation (poly(ADP-ribose) polymer is denoted "pADPr"). N-terminal domain of PARP-1 protein serves as a sensor of the double stranded breaks or nicks in genomic DNA. Upon binding of damaged DNA it mediates conformational changes which leads to disruption of interaction with histones and consequently to the activation of PARP-1 enzymatic reaction. Part 3 shows DNA-independent PARP-1 activation. Developmental or environmental signals induces local changes in the histone modification core and subsequently expose N-tail of histone H4 and/or hide histone H2A followed by H4-dependent PARP-1 activation.

Various terms relating to aspects of the invention are used throughout the specification and claims. Such terms are to be given their ordinary meaning in the art, unless otherwise indicated. Other specifically defined terms are to be construed in a manner consistent with the definition provided herein.

As used herein, the singular forms "a," "an," and "the" include plural referents unless expressly stated otherwise.

Inhibiting comprises reducing, decreasing, blocking, preventing, delaying, inactivating, desensitizing, stopping, and/or downregulating the biologic activity or expression of a molecule or pathway of interest. By way of example, but not of limitation, inhibiting the biologic activity of PARP-1 includes inhibiting production of poly(ADP)-ribose.

Determining may comprise any suitable quantitative or qualitative measurements, according to any suitable technique.

It has been observed in accordance with the invention that PARP-1 can be activated by interacting with core histone H4, that the catalytic domain of PARP-1 is responsible for its H4-dependent activation, and that this activation is stronger and more stable than the DNA-dependent activation of PARP-1. This observation led to development of an assay for identifying materials that inhibit PARP-1 with specificity and potency, which preferably are independent of nicotinamide adenine dinucleotide (NAD+). Inhibition of PARP-1 has implications for treatment of certain types of cancers and other diseases, disorders, or conditions that are caused by, facilitated by, exacerbated by, or otherwise involve biochemical pathways modulated or regulated by the biologic activity PARP-1. Accordingly, the disclosure features systems, methods, and kits for identifying inhibitors of the biologic activity of PARP-1. The methods preferably identify inhibitors of the H4-dependent activation of PARP-1. The disclosure also features systems, methods, and kits for detecting and/or quantifying PARP-1 in a sample. The disclosure also features systems, methods, and kits for determining the synthesis of poly(ADP)-ribose in a sample. Any of the methods may be carried out in vitro, ex vivo, or in situ.

In some aspects, the methods comprise contacting PARP-1 or a portion of the PARP-1 protein comprising the catalytic domain with a test compound, nicotinamide adenine dinucleotide (NAD), and the core histone H4, and determining the biologic activity of the PARP-1 or portion of the PARP-1 protein comprising the catalytic domain contacted with the test compound and the core histone H4 relative to the biologic activity of PARP-1 or a portion of the PARP-1 protein comprising the catalytic domain contacted with the core histone H4 alone or relative to the biologic activity of PARP-1 or a portion of the PARP-1 protein comprising the catalytic domain contacted with the core histone H4 and a compound known to have no ability to inhibit the biologic activity of PARP-1 or a portion of the PARP-1 protein comprising the catalytic domain. A diminution of the biologic activity of PARP-1 or a portion of the PARP-1 protein comprising the catalytic domain via the test compound preferably indicates that the test compound inhibits H4-dependent PARP-1 activation. The methods are preferably suitable for high-throughput screening of test compounds for the capacity to inhibit H4-dependent PARP-1 activation. The methods preferably are carried out in the absence of DNA. Test compounds include organic and inorganic chemicals, biomolecules (proteins, nucleic acids, etc.), as well as mixtures of molecules, including extracts and other complex mixtures. The methods may include washing steps.

In some aspects, the core histone H4 may be immobilized, for example, by affixing the core histone H4 to a suitable support, which may be a plate. The core histone H4 may be immobilized directly to the support, or may be immobilized via a moiety such as biotin, with avidin or streptavidin affixed to the support. In such aspects, the PARP-1 or a portion of the PARP-1 protein comprising the catalytic domain preferably is not affixed to the support, and is free in the solution. The test compound may be pre-contacted with the PARP-1 or a portion of the PARP-1 protein comprising the catalytic domain, i.e., before contacting the PARP-1 or a portion of the PARP-1 protein comprising the catalytic domain with the core histone H4 and NAD. The test compound and the core histone H4 may be contacted with the PARP-1 or a portion of the PARP-1 protein comprising the catalytic domain and with the core histone H4 and NAD substantially at the same time. The test compound may be pre-contacted with the core histone H4, i.e., before contacting the PARP-1 or a portion of the PARP-1 protein comprising the catalytic domain with the core histone H4 and NAD. Determining the biologic activity of PARP-1 or the portion of the PARP-1 protein comprising the catalytic domain may comprise determining the level of poly(ADP)-ribose produced by the PARP-1 protein or the portion of the PARP-1 protein comprising the catalytic domain. Determination of the level of poly(ADP)-ribose may be qualitative or quantitative, and may be according to any technique suitable in the art for poly(ADP)-ribose detection and/or quantification, for example, detection of light absorbance at 650 nm or 450 nm.

In some aspects, the PARP-1 or the portion of the PARP-1 protein comprising the catalytic domain may be immobilized, for example, by affixing the PARP-1 or the portion of the PARP-1 protein comprising the catalytic domain to a suitable support, which may be a plate. The PARP-1 or the portion of the PARP-1 protein comprising the catalytic domain may be immobilized directly to the support, or may be immobilized via a moiety such as biotin, with avidin or streptavidin affixed to the support. In such aspects, the core histone H4 preferably is not affixed to the support, and is free in the solution. The test compound may be pre-contacted with the PARP-1 or a portion of the PARP-1 protein comprising the catalytic domain, i.e., before contacting the PARP-1 or a portion of the PARP-1 protein comprising the catalytic domain with the core histone H4 and NAD. The test compound and the core histone H4 and NAD may be contacted with the PARP-1 or a portion of the PARP-1 protein comprising the catalytic domain substantially at the same time. Determining the biologic activity of PARP-1 or the portion of the PARP-1 protein comprising the catalytic domain may comprise determining the level of poly(ADP)-ribose produced by the PARP-1 protein or the portion of the PARP-1 protein comprising the catalytic domain. Determination of the level of poly(ADP)-ribose may be qualitative or quantitative, and may be according to any technique suitable in the art for poly(ADP)-ribose detection and/or quantification, for example, detection of light absorbance at 650 nm or 450 nm.

The interaction of PARP-1 and core histone H4 may be further used to detect and/or quantify PARP-1 in a sample. Such detection and quantification methods comprise contacting a sample with the core histone H4 in the presence of nicotinamide adenine dinucleotide, and determining the level of H4-dependent biologic activity of PARP-1 in the sample. Determining the level of H4-dependent biologic activity of PARP-1 may comprise determining the level of poly(ADP)-ribose. Determining the level of poly(ADP)-ribose may comprise measuring light absorbance at 450 nm or 650 nm. The methods may comprise determining the quantity of PARP-1 in the sample. The sample may comprise a cell extract. The cell extract may comprise a cancer cell extract. The cancer cell extract may comprise a prostate cancer cell extract, a kidney cancer cell extract, a breast cancer cell extract, a leukemia cell extract, a melanoma cell extract, a lymphoma cell extract, a glioblastoma cell extract, or an ovarian cancer cell extract. The sample may be treated with an enzyme such as DNAse to deplete DNA in the sample, or the sample may be otherwise treated to remove DNA from the sample. The methods may optionally comprise depleting DNA from the sample.

The synthesis of poly(ADP-ribose) in a sample may also be determined and/or quantified. Such methods comprise contacting a sample with the core histone H4 in the presence of nicotinamide adenine dinucleotide, and determining the level of poly(ADP)-ribose in the sample. The core histone H4 may be affixed to a support. Determining the level of poly(ADP)-ribose may comprise measuring light absorbance at 450 nm or 650 nm. The sample may comprise a cell extract. The cell extract may comprise a cancer cell extract. The cancer cell extract may comprise a prostate cancer cell extract, a kidney cancer cell extract, a breast cancer cell extract, a leukemia cell extract, a melanoma cell extract, a lymphoma cell extract, a glioblastoma cell extract, or an ovarian cancer cell extract. The sample may be treated with an enzyme such as DNAse to deplete DNA in the sample, or the sample may be otherwise treated to remove DNA from the sample. The methods may optionally comprise depleting DNA from the sample.

Also featured are systems and kits for determining PARP-1 inhibitors. The systems and kits comprise PARP-1 or a portion of the PARP-1 protein comprising the catalytic domain, nicotinamide adenine dinucleotide (NAD), and the core histone H4. In some aspects, the core histone H4 may be affixed to a support. Thus, the systems may further comprise a support, for example, a plate comprising a plurality of wells, to which the core histone H4 is affixed. The systems and kits may comprise control compounds, for example, compounds that positively inhibit H4-dependent PARP-1 activation such that the compounds inhibit the biologic activity of PARP-1 and the portion of the PARP-1 protein comprising the catalytic domain such that PARP-1 and the portion of the PARP-1 protein comprising the catalytic domain do not produce poly(ADP) ribose. Other control compounds may include compounds that do not inhibit H4-dependent PARP-1 activation such that the compounds do not inhibit the biologic activity of PARP-1 and the portion of the PARP-1 protein comprising the catalytic domain such that PARP-1 and the portion of the PARP-1 protein comprising the catalytic domain remain capable of producing poly(ADP) ribose.

The systems and kits may further comprise instructions for using the PARP-1 or a portion of the PARP-1 protein comprising the catalytic domain, nicotinamide adenine dinucleotide (NAD+), and the core histone H4 in a method for identifying inhibitors of the biologic activity of PARP1, including any of the methods described or exemplified herein. The instructions may include instructions for parallel screening of the positive and negative control compounds, for comparison against screening of test compounds as part of the method. The systems and kits preferably do not include any DNA such that a screening method is capable of being carried out to screen the DNA-independence of the test compound in inhibiting the biologic activity of PARP-1.

The following examples are provided to describe the invention in greater detail. They are intended to illustrate, not to limit, the invention.

Example 1

Two Pathways of the PARP-1 Protein Activation

It was observed that interacting with core histones in nucleosomes, the PARP-1 protein becomes broadly distributed in chromatin. PARP-1 is inactive in this state, because of the inhibitory effect of histone H2A (FIG. 1, part 1). Two pathways of PARP-1 activation have been identified: (1) DNA-dependent PARP-1 activation (FIG. 1, part 2), and (2) H4-dependent PARP-1 activation (FIG. 1, part 3). In the second activation pathway, developmental and environmental signals induce local changes in the histone modification core and subsequently expose the N-tail of histone H4 and/or hide histone H2A, followed by H4-dependent PARP-1 activation.

Example 2

H4-Dependent PARP-1 Activation is Stronger than DNA-Dependent Activation

The two pathways described in Example 1 can be separated in vitro by cleaving Zn-fingers from the PARP-1 protein using caspase 3. This isoform of PARP-1 can be still activated by H4, but not by DNA (FIG. 2, panel A). It was found that nucleosomal histones control PARP-1 protein activity. Specifically, H4 activates PARP-1 (FIG. 2, panel B), while histones H2B, H2A, H2Av (and phospho-mutant isoform H2AvSE) inhibit PARP-1 with variable degrees of effectiveness (FIG. 2, panel C). Although histones H2Av and H2AvSE inhibit PARP-1 by themselves, when contained inside of a nucleosome they facilitate PARP-1 interaction with H4 and thereby activate PARP-1 (FIG. 2 panel D). Activation of PARP-1 by H4 is stronger and produces significantly more pADPr than the DNA-dependent activation route (FIG. 2, panel A). Without intending to be limited to any particular theory or mechanism of action, it is believed that interactions with histones play an important for PARP-1 activation in vivo in genotoxic stress response and in transcriptional pathways.

Example 3

The H4-Dependent PARP-1 Activation Pathway Requires the Catalytic Domain of PARP-1 (C-PARP) Only Histone variant H2Av controls PARP-1 targeting to promoters. The data show that the C-terminal domain of PARP-1 (the catalytic domain) is responsible for binding to histones and is sufficient for the PARP-1 activation by H4. The DNA-binding and auto-modification domains are not required for its activation (FIG. 3A-D). Previously, it was found that PARP-1 localizes to chromatin domains containing H2Av nucleosomes. Although PARP-1 lacks any significant ability to bind H2Av (FIG. 3B), it is believed to be possible that the relatively more open structure of H2Av nucleosome allows for a greater accessibility of H3 and H4 for binding with PARP-1. H4-dependent PARP-1 activation requires only the catalytic domain of PARP-1 (C-PARP), which is easier to produce and is believed to be more stable in vitro.

Example 4

Screening Strategy

Figure 5:
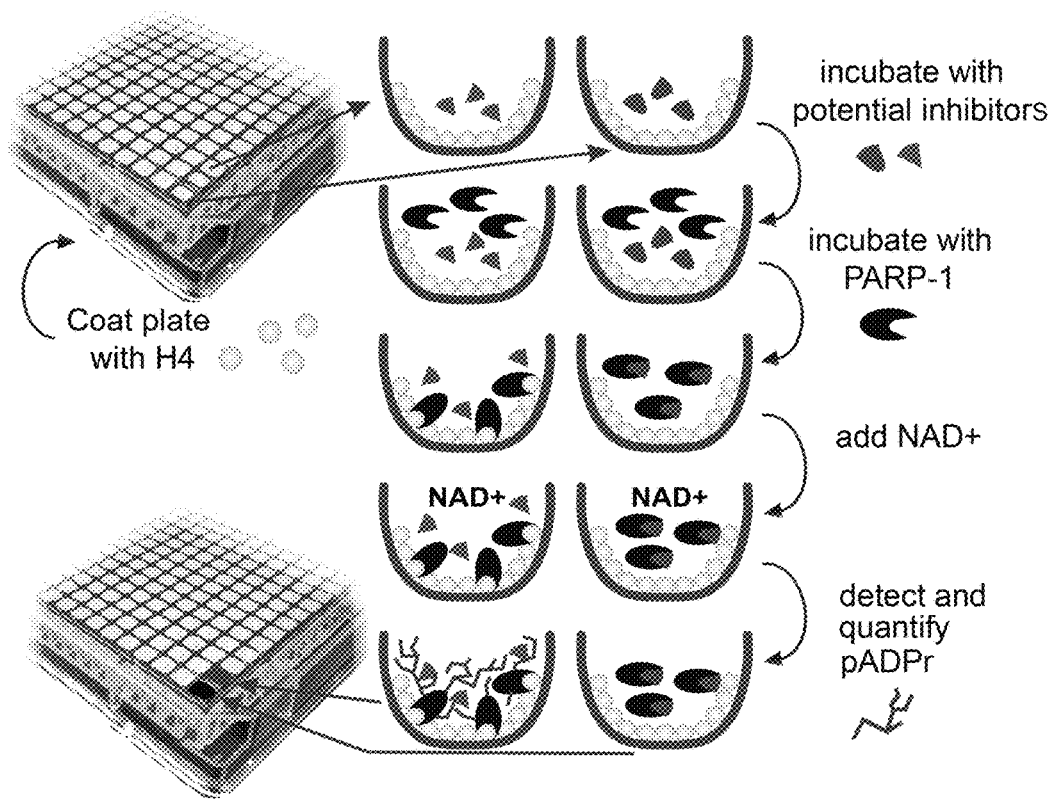
FIGS. 5A and 5B show a cartoon representation of the assay principle, with compounds that obstruct the ability of PARP-1 to interact with immobilized H4 (left side, compounds represented by triangles, PARP-1 represented by circle), and with compounds unable to obstruct PARP-1 and H4 interaction (right side, compounds represented by plus sign).

A PARP-1 activation screening assay was designed using a 384-well ELISA plate coated with histone H4 protein-activator. PARP-1 reactions were set up in each well in presence of single a small molecule compound or a positive and a negative control. The product of these reactions, poly-(ADP)-ribose, was quantified. Absorbance at 650 or 450 nm was used as an indicator of PARP-1 activity (FIG. 4A-4D). The assay measured inhibition of PARP-1 with the immobilized H4 by the small molecule test compounds, as a function of poly-(ADP)-ribose production. A representation of the inhibition concept is provided in FIG. 5.

The screening assay was validated using a test library in a pilot screen. The test library was the ICCB Known Bioactives library of 480 compounds was used, which includes all popular PARP-1 inhibitors.

In addition to all known PARP-1 inhibitors, the pilot screening of this test library identified seven molecules previously unknown as PARP-1 inhibitors. Following the pilot screen, a large analysis of 50,000 small compounds was carried out, and positive hits which reduced PARP-1 activity by at least 3-fold were selected. Nine hundred three small molecules inhibiting PARP-1 were identified in this cell-free system. After eliminating redundancies that display negligible structural differences, 639 of selected compounds were re-analyzed, confirming that all strong positive hits were 100% reproducible. 373 small molecules in this list inhibited PARP-1 at the same or better level than commonly used PARP-1 inhibitors 4-ANI and PJ34. A large number of the newly identified PARP-1 inhibitors demonstrated obvious structural similarities to the known PARP-1 inhibitors. A computation approach was employed to narrow down the list of small molecules for further analysis.

The invention is not limited to the embodiments described and exemplified above, but is capable of variation and modification within the scope of the appended claims.

I claim:

1. A method for screening a compound for capability to inhibit poly(ADP-ribose) polymerase 1 (PARP-1), comprising contacting a portion of PARP-1 comprising the catalytic domain with core histone H4 in the presence of the compound and nicotinamide adenine dinucleotide, wherein the portion is the product of caspase 3 cleavage of the full length PARP-1 protein, wherein the core histone H4 is immobilized on a plate comprising a plurality of wells; and determining the level of H4-dependent biologic activity of the portion of PARP-1 comprising the catalytic domain in the presence of the compound relative to the level of H4-dependent biologic activity of the portion of PARP-1 comprising the catalytic domain in the absence of the compound.

2. The method of claim 1, wherein the compound is contacted with the portion of PARP-1 comprising the catalytic domain prior to contacting the portion of PARP-1 comprising the catalytic domain with the core histone H4.

3. The method of claim 1, wherein the core histone H4 is contacted with the compound prior to contacting the portion of PARP-1 comprising the catalytic domain with the core histone H4.

4. The method of claim 1, wherein the determining of the level of H4-dependent biologic activity of the portion of PARP-1 comprising the catalytic domain comprises determining the level of poly(ADP)-ribose produced by the portion of PARP-1 comprising the catalytic domain.

5. The method of claim 4, wherein determining the level of poly(ADP)-ribose comprises quantifying the level of poly(ADP)-ribose.

6. A kit for screening a compound for capability to inhibit poly(ADP-ribose) polymerase 1 (PARP-1), comprising:
a portion of PARP-1 comprising the catalytic domain, wherein the portion is the product of caspase 3 cleavage of the full length PARP-1 protein;
nicotinamide adenine dinucleotide;
core histone H4 immobilized on a plate comprising a plurality of wells; and instructions for using the kit.

7. The kit of claim 6, wherein the a portion of PARP-1 comprising the catalytic domain is free of DNA.

8. The kit of claim 6, further comprising a control compound that inhibits H4-dependent activation of PARP-1.

9. The kit of claim 6, further comprising a control compound that does not inhibit H4-dependent activation of PARP-1.

10. The kit of claim 6, wherein the core histone H4 is affixed to the plate directly or via biotin/avidin or biotin/streptavidin.

* * * * *

UNITED STATES PATENT AND TRADEMARK OFFICE
CERTIFICATE OF CORRECTION

| | |
|---|---|
| PATENT NO. | : 10,472,664 B2 |
| APPLICATION NO. | : 14/870516 |
| DATED | : November 12, 2019 |
| INVENTOR(S) | : Alexei Tulin |

It is certified that error appears in the above-identified patent and that said Letters Patent is hereby corrected as shown below:

In the Specification

Column 1, between the CROSS REFERENCE TO RELATED APPLICATIONS and FIELD OF THE INVENTION Sections, add the following section heading and paragraph:
--STATEMENT OF GOVERNMENT SUPPORT
This invention was made with government support under GM077452, and DK082623 awarded by the National Institutes of Health. The government has certain rights in the invention.--

Signed and Sealed this
Fifth Day of September, 2023

Katherine Kelly Vidal
*Director of the United States Patent and Trademark Office*